US006808932B1

(12) United States Patent
Shackleton

(10) Patent No.: US 6,808,932 B1
(45) Date of Patent: Oct. 26, 2004

(54) DIAGNOSIS OF SMITH-LEMLI-OPTIZ SYNDROME

(75) Inventor: Cedric Shackleton, Berkeley, CA (US)

(73) Assignee: Children's Hospital & Research Center at Oakland, Oakland, CA (US)

(*) Notice: Subject to any disclaimer, the term of this patent is extended or adjusted under 35 U.S.C. 154(b) by 430 days.

(21) Appl. No.: 10/077,577

(22) Filed: Feb. 15, 2002

(51) Int. Cl.[7] .............................................. G01N 24/00

(52) U.S. Cl. ...................... 436/87; 436/173; 436/177; 436/811; 436/71; 436/139; 436/817

(58) Field of Search ........................ 436/87, 173, 177, 436/811, 71, 139, 817

(56) References Cited

U.S. PATENT DOCUMENTS 5,629,210 A * 5/1997 Hercules et al. .............. 436/71

FOREIGN PATENT DOCUMENTS

WO    WO 01/92893    12/2001

OTHER PUBLICATIONS

Abuelo, et al. "Prenatal detection of the cholesterol biosynthetic defect in the Smith–Lemli–Opitz syndrome by the analysis of amniotic fluid sterols", *Am J Med Genet,* (1995) vol. 56: 281–285.*
Andersson, et al. "Adrenal insufficiency in Smith–Lemli–Opitz Syndrome", *Am. J. Med Genet,* (1999) vol. 82 (5): 382–384.*
Bradley, et al. "Levels of unconjugated estriol and other maternal serum markers in pregnancies with Smith–Lemli–Opitz (RSH) syndrome fetuses", *Am J Med Genet.* (1999) vol. 82: 355–358.*
Clayton. "Disorders of cholesterol biosynthesis", *Arch. Dis. Child,* (1998) vol. 78: 185–189.*

Dallaire, et al. "Prenatal diagnosis of Smith–Lemli–Opitz syndrome is possible by measurement of 7–dehydrocholesterol in amniotic fluid", *Prenat. Diagn.,* (1995) vol. 15: 855–858.*
Donnai, et al. "The lethal multiple congenital anomaly syndrome of polydactyly, sex reversal, renal hypoplasia, and unilobular lungs", *J. Med. Genet.* (1986) vol. 23: 64–71.*
Li–Wei Guo, et al. "Synthesis of Ring B Unsaturated Estriols. Confirming the Structure of a Diagnostic Analyte for Smith–Lemli–Opitz Syndrome." (2001) Organic Letters. vol. 3.*
Wassif et al., "Mutations In the Human Sterol$\Delta^7$–Reductase Gene at 11q12–13 Cause Smith–Lemli–Opitz Syndrome," Am. J. Hum. Genet. 63:55–62, 1998.*
Fitzky, et al. "Mutations in the delta–7–sterol reductase gene in patients with the Smith–Lemli–Opitz syndrome", *Proc. Natl. Acad. Sci. USA,* (1998) vol. 95: 8181–8186.
Glass, et al. "Steroid sulphatase deficiency is the major cause of extremely low oestriol production at mid–pregnancy. A urinary steroid assay for the discrimination of steroid sulphatase deficiency from other causes", *Prenat. Diagn.,* (1998) vol. 18: 789–800.

(List continued on next page.)

*Primary Examiner*—Jill Warden
*Assistant Examiner*—Monique T. Cole
(74) *Attorney, Agent, or Firm*—Carol L. Francis; Bozicevic, Field & Francis LLP

(57) ABSTRACT

The invention provides a non-invasive assay for the detection of a SLOS affected individual by determining the ratio of at least one of the specific SLOS steroid analytes, dehydro-estriol (8-DHE3) and a dehydro-pregnanetriol (7-DHPT) to their normal steroid counterparts estriol (E3) and pregnanetriol (PT), respectively. 8-DHE3 and 7-DHPT represent metabolites which accumulate in the blood and urine of an individual with SLOS or an individual carrying a SLOS affected fetus. The invention provides for a reliable and reproducible method of screening women for SLOS affected fetuses early on in pregnancy.

10 Claims, 4 Drawing Sheets

Maternal urine oestriol

Maternal urine pregnanetriol

OTHER PUBLICATIONS

Irons, et al. "Defective cholesterol biosynthesis in Smith–Lemli–Opitz syndrome", *Lancet.* (1993) vol. 341: 1414.

Irons, et al. "Prenatal diagnosis of Smith–Lemli–Opitz syndrome", *Prenat. Diagn.,* (1998) vol. 18: 369–372.

Kelley. "Inborn errors of cholesterol biosynthesis", *Adv. Pediat.,* (2000) vol. 47: 1–53.

Kratz, et al. "Prenatal diagnosis of the RSH/Smith–Lemli–Opitz syndrome", Am. J. Med. Genet. vol. 82: 376–381 (1999).

Mcgaughran, et al. "Prenatal diagnosis of Smith–Lemli–Opitz syndrome", *Am. J. Med. Genet.,* (1995) vol. 56: 269–271.

Mckeever, et al. "Smith–Lemli–Opitz syndrome II: A disorder of the fetal adrenals?", *J. Med. Genet.,* (1990) vol. 27: 465–466.

Mills, et al. "First trimester prenatal diagnosis of Smith–Lemli–Opitz syndrome (7–dehydrochloesterol) reductase deficiency", *Pediatr. Res.,* (1996) vol. 39: 816–819.

Moebius, et al. "Molecular cloning and expression of the human delta 7–sterol reductase", *Proc. Natl. Acad. Sci. USA,* (1998) vol. 95: 1899–1902.

Palomaki, et al. "Maternal serum screening for Down syndrome in the United States: A 1995 survey", *Am. J. Med. Genet.,* (1997) vol. 176: 1046–1051.

Rossiter, et al. "Smith–Lemli–Opitz Syndrome: Prenatal diagnosis by quantification of cholesterol precursors in amniotic fluid", *American Journal of Medical Genetics,* (1995) vol. 56: 272–275.

Shackleton. "Mass spectrometry in the diagnosis of steroid–related disorders and in hypertension research", *J. Steroid Biochem. Molec. Biol.,* (1993) vol. 45: 127–140.

Shackleton, et al. "Equine type estrogens produced by a pregnant woman carrying a Smith–Lemli–Opitz syndrome fetus", *J. Clin. Endrocrinol. Metab.,* (1999) vol. 84: 1157–1159.

Shackleton, et al. "Midgestational maternal urine steroid markers of fetal Smith–Lemli–Opitz syndrome (7–dehydrocholesterol 7–reductase deficiency)", *Steroids,* (1999) vol. 64: 446–452.

Shackleton, et al. "Neonatal urinary steroids in Smith–Lemli–Opitz Syndrome associated with 7–dehydrocholesterol reductase deficiency", *Steroids,* (1999) vol. 64: 481–490.

Shackleton, et al. "Dehydro–oestriol and dehydropregnanetriol are candidate analytes for prenatal diagnosis of Smith–Lemli–Opitz syndrome", *Prenat. Diagn.,* (2001) vol. 21: 207–212.

Sharp, et al. "First–trimester diagnosis of Smith–Lemli–Opitz syndrome", *Prenat. Diagn.,* (1997) vol. 17(4): 355–361.

Smith, et al. "A newly recognized syndrome of congenital nomalies", *J. Pediat.,* (1964) vol. 64: 210–221.

Steiner, et al. "Smith–Lemli–Opitz syndrome", *eMedicine J.,* (Apr. 4, 2001) vol. 2(4).

Steiner, et al. "Smith–Lemli–Opitz syndrome", *eMedicine J.,* (Feb. 5, 2002) vol. 3(2).

Tint, et al. "Defective cholesterol biosynthesis associated with the Smith–Lemli–Opitz syndrome", *N. Engl. J. Med.,* (1994) vol. 330: 107–113.

Tint, et al. "Fetal Smith–Lemli–Opitz syndrome can be detected accurately and reliably by measuring amniotic fluid dehydrocholesterols", *Prenat. Diagn.,* (1998) vol. 18: 651–658.

Waterham, et al. "Smith–Lemli–Opitz Syndrome is Cuased by Mutations in the 7–Dehydrocholesterol Reducatse Gene", *Am. J. Hum. Genet.,* (1998) vol. 63: 329–338.

* cited by examiner

Maternal urine pregnanetriol
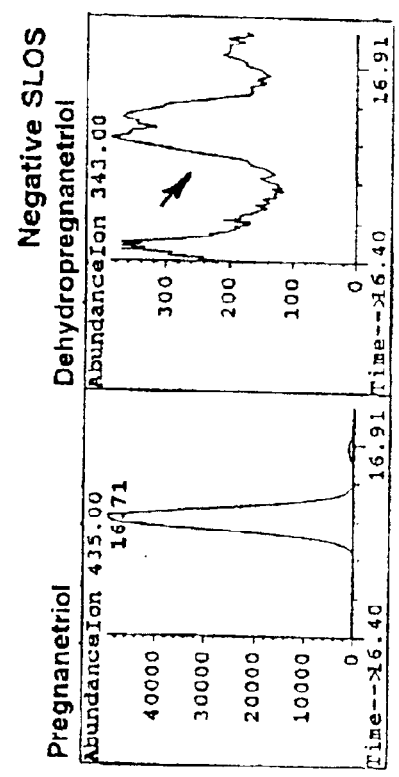
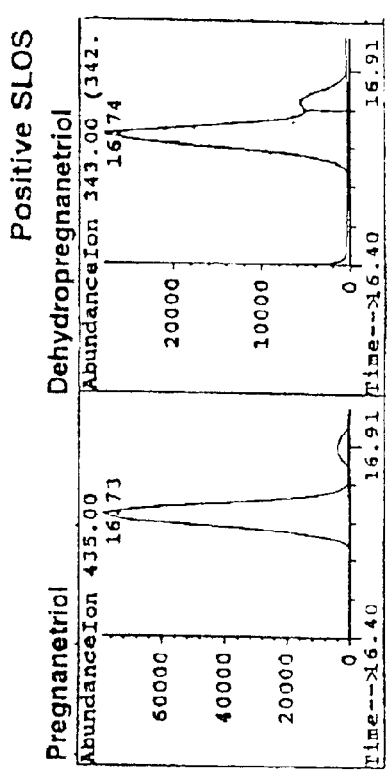
Maternal urine oestriol
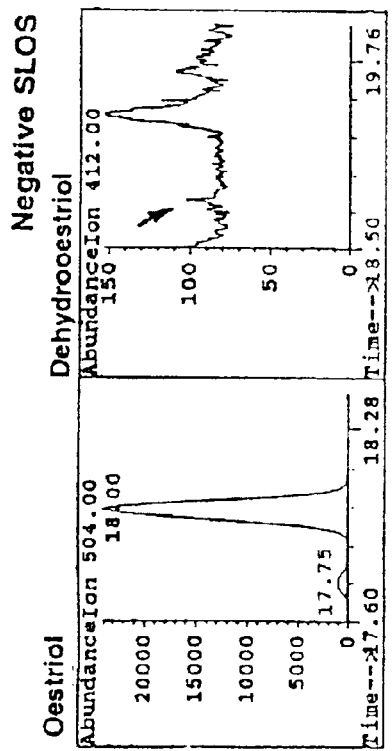
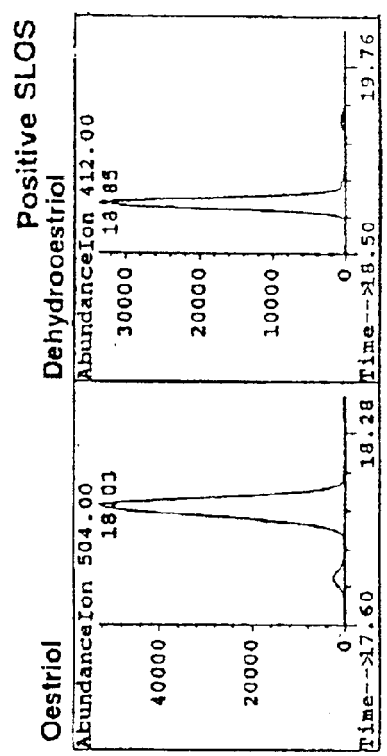
Figure 1

*FIGURE 2*

Steroid Urine Concentrations (µg/g creatinine), Serum uE₃ and Diagnostic Ratios in Patients At Risk for SLOS

| | P1[a] | P2 | P3 | P4 | P5 | P1-P5 MEAN | N1 | N2 | N3 | N4 | N5 | N6 | N7 | N8 | N1-N8 MEAN |
|---|---|---|---|---|---|---|---|---|---|---|---|---|---|---|---|
| DHC/Chol[c] (%) | 83.8 | 176.2 | 54.0 | 22.5 | 130 | 93.3 | 0.01 | .006 | .0012 | .006 | .001 | .23 | 0.21 | 0.02 | 0.06 |
| uE₃[b] (MOM) | 0.23 | 0.19 | NM[d] | NM | 0.14 | 0.19 | 1.09 | 0.79 | 0.83 | 1.59 | 1.07 | 1.17 | 1.76 | 1.12 | 1.18 |
| Gestational Age (weeks) | 20 | 31 | 20 | 12 | 18 | 20 | 16 | 15 | 15 | 17 | 17 | 17 | 15 | 16 | 16 |
| Pregnanediol (PD) | 4485 | 10545 | 21014 | 5981 | 7903 | 9985 | 3882 | 3014 | 6319 | 6892 | 15757 | 5858 | 5469 | 12069 | 7407 |
| Pregnanetriol (PT) | 460 | 444 | 838 | 583 | 398 | 545 | 388 | 414 | 638 | 778 | 1666 | 873 | 1137 | 1419 | 914 |
| 7-DHPT | 470 | 160 | 513 | 21.5 | 340 | 301 | <1.0 | <2.7 | <1.9 | <3.1 | <4.7 | <4.4 | <2.8 | <3.0 | <3.0 |
| Oestriol (E₃) | 142 | 485 | 198 | 67.5 | 285 | 235 | 1561 | 426 | 1274 | 3227 | 8466 | 5168 | 928 | 8397 | 3680 |
| 8-DHE₃ | 196 | 779 | 194 | 4.5 | 325 | 300 | <2.2 | <5.0 | <1.0 | <1.1 | <10.6 | <3.4 | <4.0 | <8.0 | <4.6 |
| 8-DHE₃/E₃ | 1.38 | 0.73 | 0.98 | 0.07 | 1.14 | 0.86 | <.001 | <.01 | <.008 | <.0005 | <.003 | <.0007 | <.004 | <.001 | <.004 |
| 7-DHPT/PT | 1.02 | 0.35 | 0.59 | 0.04 | 0.82 | 0.36 | <.001 | <.01 | <.003 | <.005 | <.003 | <.007 | <.003 | <.002 | <.005 |
| E₃/PD (%) | 6.3 | 12.0 | 1.6 | 2.8 | 8.0 | 6.2 | 40.2 | 14.1 | 20.1 | 47.0 | 53.7 | 88.2 | 17.0 | 69.6 | 43.7 |
| 8-DHE₃+E₃/PD (%) | 13.0 | 21.0 | 3.3 | 3.0 | 16.8 | 11.4 | 40.2 | 14.1 | 20.1 | 47.0 | 53.7 | 88.2 | 17.0 | 69.6 | 43.7 |

Notes: [a]Patients, P = positive for SLOS, N = negative for SLOS.
[b]unconjugated serum oestriol reported as multiples of median (MOM).
[c]DHC = 7-dehydrocholesterol. All values from amniotic fluid analysis with exception of P4, N3 and N7 which were from chorionic villus cells.
[d]NM = not measured.

FIGURE 3

Free and Conjugated Pregnanes and Oestriols in Serum (ng/ml)

| | P2[1] | N2 | N3 | N4 | N5 | N6 | N1-N6 MEAN |
|---|---|---|---|---|---|---|---|
| Pregnanediol (PD) | 310 | 119 | 74 | 178 | 109 | 118 | 119 |
| Pregnanetriol (PT) | 25 | 39 | 15 | 30 | 44 | 28 | 31 |
| 7-DHPT | 3.4 | ≤0.1 | ≤0.05 | ≤0.1 | ≤0.15 | ≤0.45 | ≤0.17 |
| Estriol (E$_3$) | 26 | 66 | 29 | 13 | 6.0 | 17 | 26 |
| 8-DHE$_3$ | 5.3 | ≤.66 | ≤.64 | ≤.11 | ≤.17 | ≤0.13 | ≤0.34 |
| 7-DHPT/PT | 0.13 | ≤.003 | ≤.01 | ≤.003 | ≤.004 | ≤.02 | ≤0.008 |
| 8-DHE$_3$/E$_3$ | 0.20 | ≤.01 | ≤.02 | ≤.008 | ≤.03 | ≤.007 | ≤0.014 |

Notes: [1] P = positive for SLOS; N = negative for SLOS.

DIAGNOSIS OF SMITH-LEMLI-OPTIZ SYNDROME

GOVERNMENT RIGHTS

This invention was made with government support under federal grant nos. R03-HD39707 awarded by National Institute of Health. The United States Government may have certain rights in this invention.

FIELD OF THE INVENTION

The present invention relates to the field of diagnosis of hereditary conditions such as Smith-Lemli-Optiz syndrome, particularly prenatal diagnosis.

BACKGROUND OF THE INVENTION

Smith-Lemli-Optiz/RSH syndrome (SLOS) is a genetic disorder that affects the development of children both before and after birth SLOS affects about 1:20,000 individuals. The syndrome was first described in 1964 in three boys with poor growth, developmental delay, and a common pattern of congenital malformations including cleft palate, genital malformations, and polydactyly (extra fingers and toes). In 1993 scientists discovered that children with SLOS are unable to make sufficient cholesterol.

The Smith-Lemli-Opitz syndrome (SLOS) is caused by impaired activity of the enzyme 3β-hydroxsterol, $\Delta^7$-reductase (7DHCR)(Irons et al., *Lancet* 341: 1414, 1993; Tint et al., *N Engl J Med* 330: 107–113, 1994), which is involved in the enzymatic conversion of 7-dehydrocholesterol to cholesterol in one of two proposed routes of cholesterol biosynthesis (Scheme 1). The defect in 7DHCR results in an abnormal accumulation of 7- and 8-dehydrocholesterol (1 and 2). More than 60 enzyme mutations have been detected in SLOS-affected individuals (Fitzky et al., *Proc Natl Acad Sci USA* 95; 8181–8186, 1998; Moebius et al., *Proc Natl Acad Sci USA* 95: 1899–1902, 1998; Wassif et al., *Am J Hum Genet* 63: 329–338, 1998).

Scheme 1
Conversion of fetal $\Delta^{5,7}$ and $\Delta^{5,8}$ sterols to cholesterol

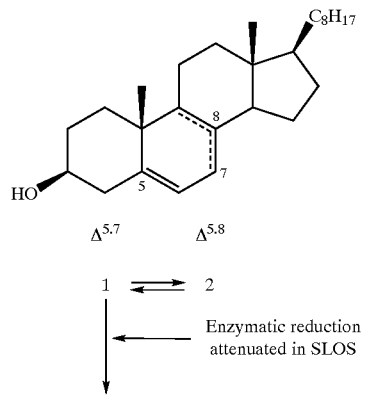

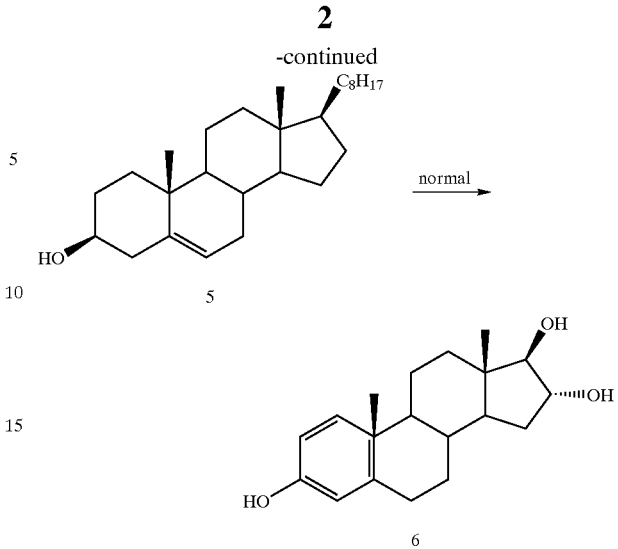

The challenge in prenatal diagnosis has been the identification of a non-invasive test that involves detection of definitive and SLOS-specific analyte(s), and which can be performed early in pregnancy. Many of the conventional SLOS screening assays involve detecting varying levels of 7-DHC, cholesterol or estriol ($E_3$) or a combination thereof, in chorionic villus (CV) or amniotic fluid samples, each of which are invasive tests and can pose a risk to the fetus. TABLE 1 lists the most common conventional SLOS markers for the screening of SLOS affected fetuses.

Table 1: Exemplary SLOS Markers
  Low Cholesterol levels in CV biopsies and amniotic fluid.
  Increased 7-DHC levels (Dehydrocholesterol) in CV and amniotic fluid.
  Increased 8-DHC levels (dehydrocholesterol II) in CV and amniotic fluid.
  Low unconjugated estriol levels in serum (non-specific marker)

Since fetal cholesterol is a precursor to estriol ($E_3$), $E_3$ is decreased in SLOS affected pregnancies (Donnai et al., *J Med Genet* 23: 6471, 1986; McKeever and Young, *J Med Genet* 27: 465466, 1990; Abuelo et al., *Am J Med Genet* 56: 281–285, 1995; Rossiter et al., *Am J Med Genet* 56: 272–275, 1995). However, detection of $E_3$ levels is not specific for SLOS-affected pregnancies. Currently, unconjugated scrum estriol ($uE_3$) is measured in about 50% of all United States pregnancies as part of the "triple marker screening" for chromosomal aneuploidies and neural tube defects (Palomaki et al., *Am J Med Genet* 176: 1046–1051, 1997). In 1999, Bradley and co-workers (Bradley et al., *Amer. J. Med. Gen.* 82:355–358, 1999) published a retrospective study of 26 SLOS pregnancies in which $uE_3$ in serum had been measured and determined that the mean $uE_3$ level was 0.23 of normal median (multiples of the median, MOM). Assaying for low estriol levels in maternal serum $MsuE_3$ along with sonography have also been suggested for diagnosing RSHISLOS (Kratz, L. E., Kelley, R. I., *Amer. J. Med. Gen.* 82:376–381, 1999) as well as identifying patients with low maternal urinary levels of estriol (McKeever and Young, 1990) at mid-gestation.

Many SLOS diagnostic methods have been suggested in which the level of 7-DHC is detected due to the increase of this cholesterol precursor in SLOS affected patients. High levels of 7-DHC and 8-DHC have been detected in amniotic fluid and in CV biopsies of SLOS patients (Rossiter, J. P. et al., *Amer. J. Med. Gen.* 56:272–275, 1995; Tint, G. S. et. al.,

*Prenat. Diagn.* 18:651–658, 1998; Irons, M. B., Tint, G. S., *Prenat. Diagn.* 18:369–372, 1998; Kratz, L. E., Kelley, R. I., *Amer. J. Med. Gen.* 82:376–381, 1999). High levels of 7-DHC have also been detected in CV biopsies of SLOS patients as early as the first trimester (Sharp, P. et al., *Prenat. Diagn.*, 17(4): 355–361, 1997). In addition to detection of 7-DHC and 8-DHC, high levels of lathosterol (cholest-7-en-3beta-ol), a 7-DHC precursor, have also been detected in amniotic fluid.

Mills, K. et al., *Pediatric Research* 39(5): 816–819 (1996) describe a method for detecting SLOS by determining the ratio of 7-DHC (a cholesterol precursor) to cholesterol in chorionic villus (CV) samples. Mills et al. determined that cholesterol synthesis via 7-DHC occurs in the placenta and/or fetus at 10 weeks of gestation and that prenatal diagnosis by CV biopsy is possible. While this test can detect SLOS early in gestation, CV biopsy is an invasive procedure and is associated with some risk to the fetus and patient.

Recently, it was shown that mid-gestational urine from a SLOS affected pregnancy contains metabolites unsaturated analogs of the compounds estriol ($E_3$) and pregnanetriol (PT). These compounds were suggested to be synthesized or metabolized from fetal 7- or 8-DHC (Shackleton et al., *Steroids.* 1999a, 64(7): 446–52; Shackleton et al., *J. Clin. Endocrinol. Metab.* 1999b, 84(3): 1157–9; Shackleton et al., *Steroids.* 1999c, 64(7): 481–90).

Shackleton et al 1999a, disclose that either 7-DHPT or 8-DIPT of the 3,16,20 and 3,17,20 (triol structures) series was present in the maternal urine of one healthy 35 year-old women carrying a SLOS fetus at 17 weeks gestation. The authors provisionally characterize the SLOS metabolite as 5β-pregn-7(or 8-)-ene-3α,17α,20α-triol; 5β-pregn-7(or 8-)-ene-3α,16α,20α-triol; 5α-pregn-7(or 8-)-ene-3α, 16α,20α-triol; 5α-pregn-7(or 8-)-ene-3α,17α,20α-triol and/or 5α-pregn-7(or 8-)-ene-3β,16α,20α-triol. The authors indicated that the major SLOS metabolite compound is either 50pregn-7-ene-3α,17α,20α-triol (7-DHPT) and/or 5β-pregn-8-ene-3α,17α,20α-triol (8-DHPT). The authors did not indicate if the tentative SLOS metabolite was a mixture of the two epimers or pure 7-DHPT or 8-DHPT and no isolation of the specific compound was attempted. Furthermore, Shackleton et al. 1999a did not show detection of the analytes prior to 17 weeks gestation.

In a separate study of three young infants affected with SLOS, the authors detected a SLOS metabolite(s) and provisionally identified the compound(s) as 3β,16α-dihydroxy-5,7-pregnadien-20-one; 3β,16α-dihydroxy-5,8 (or 9-)pregnadien-20-one; homologues of 16α-hydroxy-DHEA, as well as the 7- or 8- epimer of 5β-pregnene-3α,17α,20α-triol (Shackleton et al., *Steroids.* 1999c, 64(7). 481–90). In short, while these studies narrow the possibilities of the identity of a unique SLOS analyte, they failed to confirm the identification due to the complexity of the mass spectra profile of the biological sample and the lack of appropriate reference compounds.

While these two SLOS specific metabolites were tentatively characterized by Shackleton et al., the actual structures and identification of the two SLOS specific analytes ($\Delta^7$ or $\Delta^8$) was not determined. Depending upon the sensitivity of the detection system, a detectable amount of these SLOS analyte may be found in normal patients, an assay which only detected the presence of a epimer mixture of these compounds or the wrong epimer without proper controls, could lead to a high frequency of false positives and false negatives, making the assay unpredictable, unreliable and not commercially viable. These risks of false positives and false negatives are further exacerbated when one considers that low levels of SLOS analyte levels are found in affected SLOS individuals, thus necessitating the use of sensitive detection methods such as gas chromatography/mass spectroscopy (GC/MS).

Currently, only pregnancies at 25% risk for SLOS are routinely subjected to testing by Dehydrocholesterol (DHC) measurement, with secondary screening of SLOS based on a finding of low $E_3$ now being considered. However, since there are multiple causes of low maternal $E_3$ levels, DHC measurement in amniotic fluid or villus tissue currently remains necessary for confirming diagnosis of SLOS. Unfortunately, these methods involve the analysis of compounds which are found in substantial quantities in both normal and SLOS affected patients, making the incidence of false positives higher than may be reasonably acceptable. False positives are particularly intolerable where a fetal diagnosis of SLOS may result in the mother's decision to abort. Also, these procedures are invasive in nature, making the diagnostic testing of DHC levels, in some cases, expensive, cumbersome, impractical, and even dangerous to the fetus and mother.

Thus, there is a need to develop a sensitive, non-invasive prenatal diagnostic test utilizing a analyte specific for SLOS, which can be performed early on in gestation and which is associated with a very low possibility of false positives so as to provide a reliable diagnosis of SLOS.

SUMMARY OF THE INVENTION

The invention provides a non-invasive assay for the detection of a SLOS affected individual or SLOS-affected fetus by determining the ratio of at least one of the specific SLOS steroid analytes, dehydro-estriol (8-$DHE_3$) or dehydro-pregnanetriol (7-DHPT) to their normal steroid counterparts estriol ($E_3$) or pregnanetriol (PT), respectively. 8-$DHE_3$ and 7-DHPT represent metabolites which circulate in the blood and are excreted in urine of an individual with SLOS or an individual carrying a SLOS affected fetus. The invention provides for a reliable and reproducible non-invasive method of screening women for SLOS affected fetuses early on in pregnancy.

A primary object of the invention is a method for a diagnostic test to diagnose a fetus affected by Smith-Lemli-Optiz syndrome (SLOS) comprising obtaining a biological sample from a woman suspected of carrying an SLOS-affected fetus, analyzing the sample for at least one specific SLOS analyte and a control steroid counterpart, wherein the SLOS analyte is either 8-dehydro-estriol (8-$DHE_3$) or 5β-pregn-7-ene-α,17α,20α-triol (7-DHPT) and determining the ratio of the SLOS analyte to the control steroid counterpart found in the sample, wherein a ratio of greater than 0.01 indicates that the woman carries an SLOS-affected fetus.

Another object of the invention is to provide a non-invasive SLOS diagnostic screening method which involves analysis of a biological sample that is, for example, urine, blood, or blood-derived (e.g., plasma) from the individual to be tested.

An advantage of the method of the invention is that SLOS can be diagnosed in an affected fetus as early as 10 weeks or 11 weeks gestation.

Another advantage of the invention is that the analysis of the ratio of the SLOS analyte to the steroid counterpart minimizes the number of false positives detected.

One advantage of the diagnostic method of the present invention is that the ratio values can indicate the severity of the disorder in a particular individual. For example, a ratio of 7-DHPT/PT of 0.5 measured in one pregnancy at the 16th week would indicate a more severely affected fetus than would a ratio of 0.05, which is still considered positive for SLOS. In the first case, one half of a normally produced steroid compound is abnormal, indicating a great enzyme deficiency.

Another advantage of the diagnostic method of the invention is the omission of performing a creatinine assay on urine samples, thus simplifying the SLOS diagnostic test.

Another advantage of the invention is that a SLOS affected pregnancy can be detected by analysis of 7-DHPT/PT ratios in the first trimester. A biological sample may be obtained as early as about the 10th week of gestation, allowing for early detection of SLOS.

These and other objects, advantages, and features of the invention will become apparent to those persons skilled in the art upon reading the details of the invention as more fully described below.

BRIEF DESCRIPTION OF THE DRAWINGS

FIG. 1 is a comparison of the GC mobilities and mass spectral fragmentation of the synthetic dehydroestriols to those of the SLOS urinary metabolites.

FIG. 2 is a table of steroid urine concentrations, serum and diagnostic ratios in patients at risk for SLOS.

FIG. 3 is a table of free and conjugated pregnanes and estriols in serum of normal and affected SLOS individuals.

Figure 4:
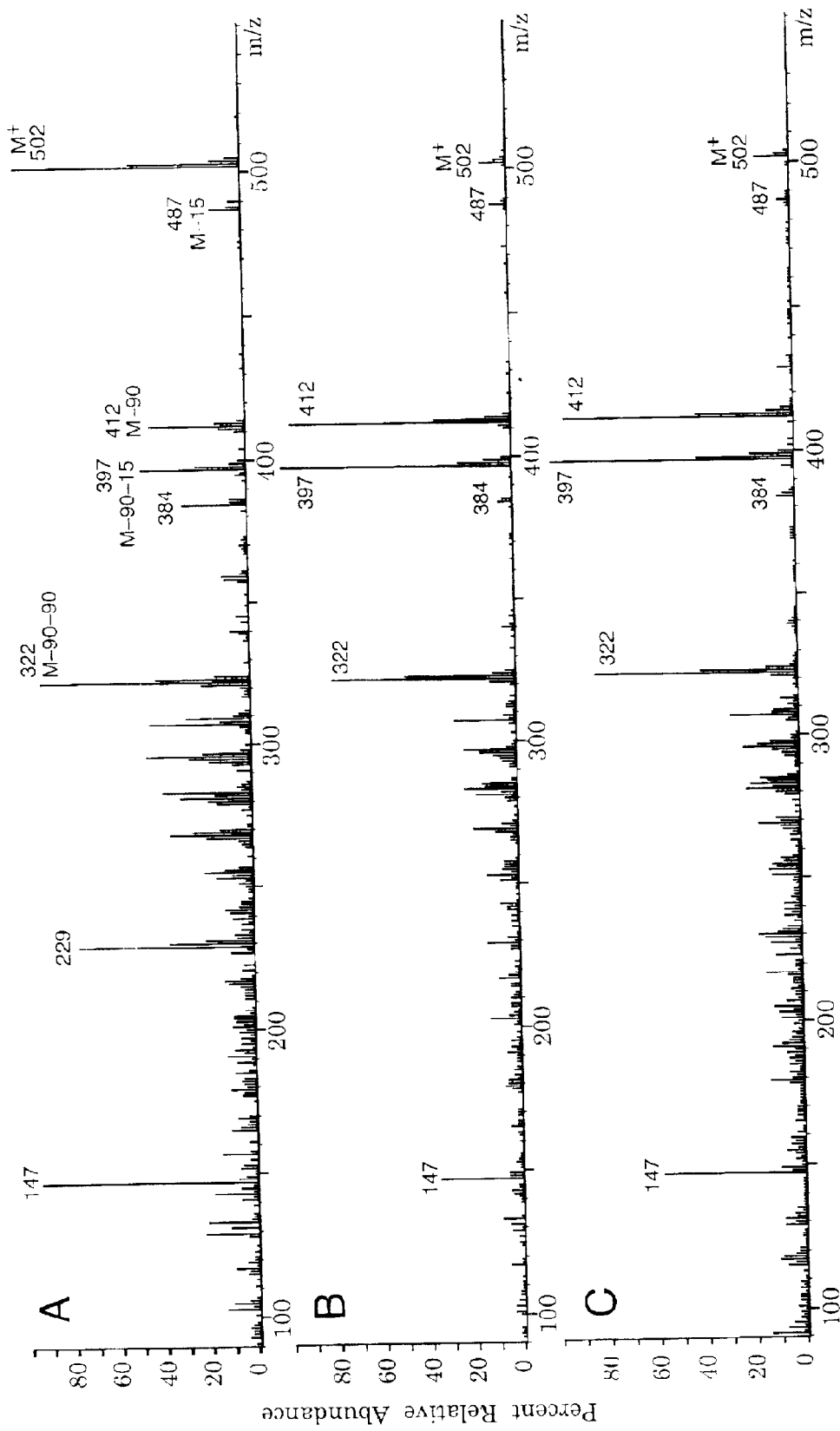
FIG. 4 is the gas chromatography/mass spectroscopy (GC/MS) spectra of tris-TMS derivatives of chemically synthesized 7-dehydroestriol (A), 8-dehydroestriol (B), and the dehydroestriol isolated from urine (C).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed its within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "the SLOS analyte" includes reference to one or more SLOS analytes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Overview

The invention is based on the discovery that certain metabolites accumulate in SLOS patients, and which, when analyzed in conjunction with their steroid counterparts, provide for specific identification of individuals with SLOS or for identification of a SLOS-affected fetus. The invention provides a method for a test prenatal diagnosis of Smith-Lemli-Optiz syndrome (SLOS) by obtaining a biological sample from a pregnant woman and analyzing the sample for 1) at least one of the following specific SLOS analytes, 8dehydro-estriol (8-DHE$_3$) or 5β-pregn-7-ene-α,17α,20α-triol (7-DHPT) and 2) a control steroid counterpart (estriol (E$_3$)and pregnanetriol (PT)), and subsequently determining the ratio of the SLOS analyte to the control steroid counterpart. A ratio of 8-DHE$_3$/E$_3$ or 7-DHPT/PT is above a predetermined threshold level is indicative of a SLOS-affected fetus.

SLOS Analytes

The invention generally involves two analytes of SLOS: 1) 8-dehydro-estriol (8-DHE$_3$) and 2) 5β-pregn-7-ene-3α, 17α,20α-triol (7-DHPT). By "SLOS analyte" is meant a compound or metabolite which is abnormally produced in patients affected with SLOS. Examples of a "SLOS analyte" are the 8-DHE$_3$ and 7-DIPT compounds, which when isolated can serve as standard compounds. "Isolated" as used herein is meant that the SLOS analyte is at least 60%, by weight, free from the naturally-occurring organic molecules with which it is naturally associated. Preferably, an isolated SLOS analyte preparation is at least 75%, more preferably at least 90%, and most preferably at least 99%, by weight, SLOS analyte. An isolated SLOS analyte may be obtained, for example, by extraction from a biological sample, or by chemical synthesis. Purity can be measured by any appropriate method, e.g., chromatography, HPLC analysis, GC/MS, and the like.

"SLOS analyte" is meant to include 8-DHE$_3$, 7-DHPT, and derivatives of 8-DHE$_3$ and 7-DHPT (e.g., which are produced during the preparation and analysis of the biological sample being analyzed). A more detailed description of each of these compounds, as well as their isolation and synthesis, is described below:
8-dehydro-estriol (8-DHE$_3$)

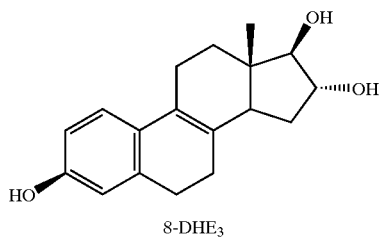

8-DHE$_3$

A Ring B unsaturated estriol has been identified by the inventors as a specific metabolite associated with SLOS which is useful in the diagnostic of Smith-Lemli-Opitz syndrome prenatally. 8-dehydro-estriol (8-DHE$_3$) is an abnormal metabolite produced in SLOS affected individuals from the high levels of dehydrocholesterols found in SLOS individuals due to the enzymatic reduction and attenuation which inhibits dehydrocholesterols to be converted to cholesterol (Scheme 2).

8-DHE$_3$ is thought to be a metabolite of the 8-dehydrocholesterol epimer which itself originates from 7-DHC through activity of an isomerase enzyme. The identification of the specific DHE$_3$ epimer associated with SLOS enables the development of SLOS diagnostic tests which are standardized and calibrated to a chemically synthesized and isolated 8-DHE$_3$ compound, further providing accuracy and reliability to the SLOS diagnostic analysis.

8-DHE$_3$ Chemical Synthesis

Considering the small amounts of material required for bioanalytical purposes, synthesis of 8-DHE$_3$ focused on partial synthesis from available estrogens, such as equilin, equilenin (10), and the Torgov diene. In a standard synthetic approach to estriols, the 16-hydroxyl is introduced by acid hydrolysis of a 16α,17α-epoxide formed from the enol acetate of estrone. However, application of this method to equilin resulted in aromatization to 16α-hydroxyequilenin. Another known approach to 16-hydroxylation entails 16-bromination of estrone, followed by hydrolysis in DMF to the ketol. Although many unsaturated 17-ketosteroids can be selectively brominated at C-16 with CuBr$_2$ in refluxing methanol, this reaction was reported to give a complex mixture for equilin. Conditions for implemented the simple ring D manipulations shown in the retrosynthetic analysis (Scheme 3) without triggering the indicated side reactions, namely aromatization of ring B, epimerization at C-14, double-bond isomerization, and ketol rearrangement.

Scheme 2
Abnormal Metabolism of fetal Δ$^{5,7}$ and Δ$^{5,8}$ sterols to either Δ7,8 dehydroestriols.

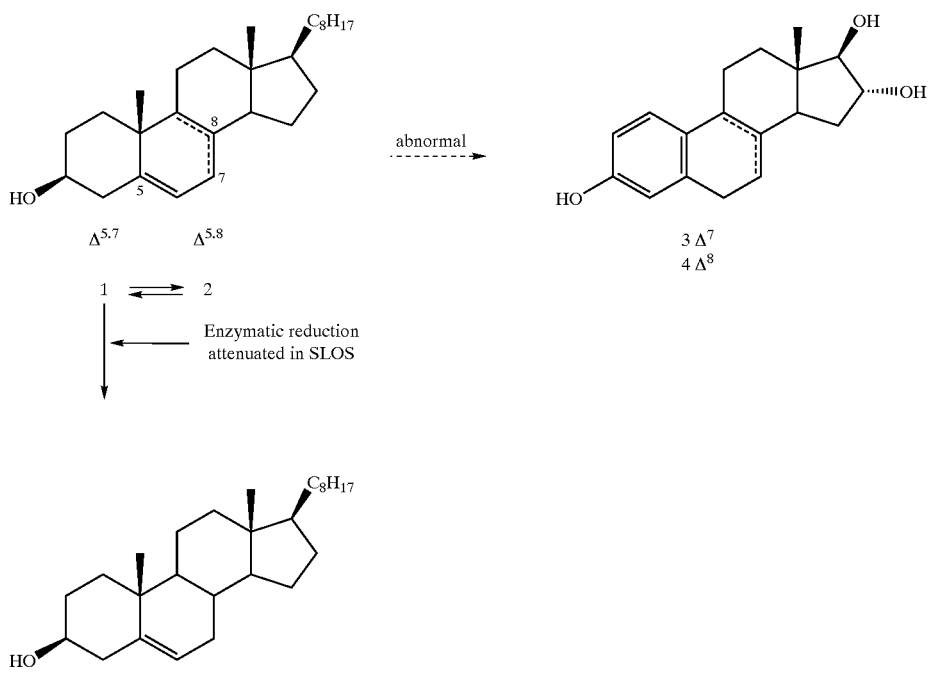

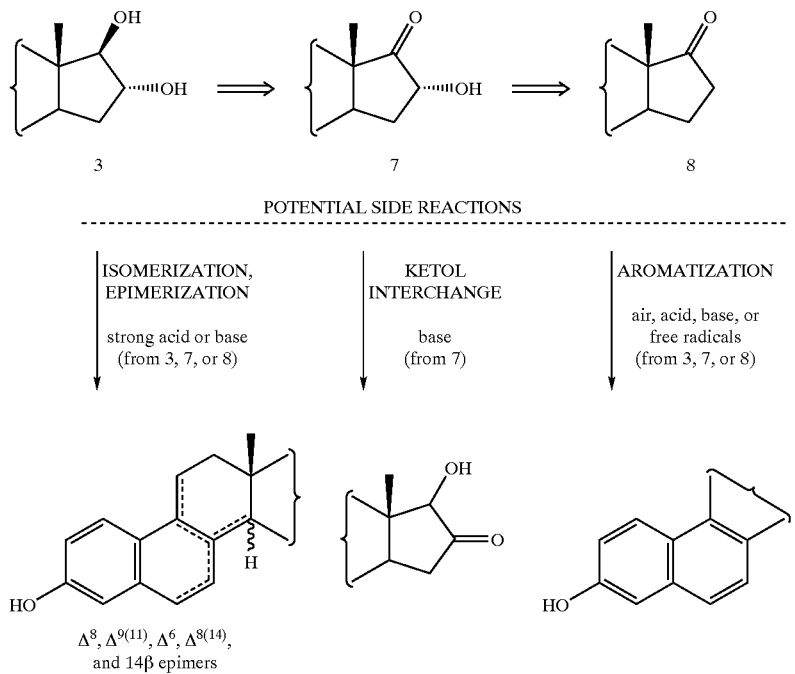

The synthesis of 8-DHE₃ was completed by converting Equilin (8) in three steps to 7-dehydroestriol, which was isomerized to 8-dehydroestriol (Scheme 4). An exemplary scheme for the synthesis of 8-DHE₃ is described in the Examples below.

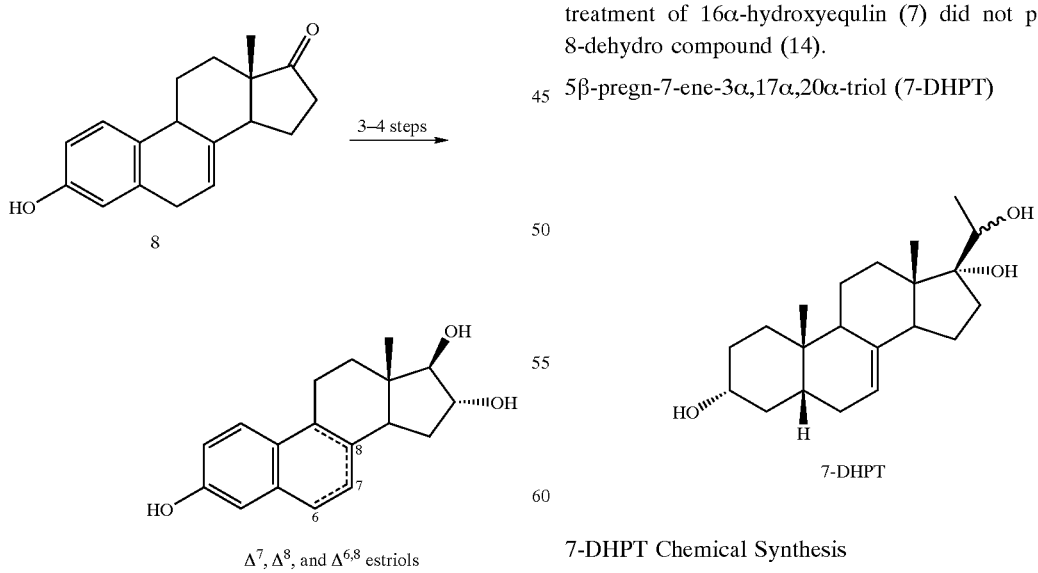

The compound 8-dehydroestriol (8-DHE₃) (14) may be prepared from various commercially available estrogens using a variety of known chemical synthetic techniques. One synthetic approach to 8-DHE₃ (14), shown in Scheme 3 and described in the following examples, utilized equilin (8). Briefly, equilin (8) was brominated to form the 16-bromoequilins (9a), (9b), which both hydrolyzed cleanly to give 16α-hydroxyequlilin (7). Sodium borohydride reduction of the 16α-hydroxyequlilin (7) yielded 7-dehydroestriol (3). Treatment of 7-dehydroestriol (3) with Li/ethylene diamine provided 8-DHE₃ (14). Notably, direct treatment of 16α-hydroxyequlin (7) did not provide the 8-dehydro compound (14).

5β-pregn-7-ene-3α,17α,20α-triol (7-DHPT)

7-DHPT Chemical Synthesis

5β-Pregn-7-ene-3α,17α,20R-triol and its 20S isomer (6a and 6b) were prepared in five steps from the commercially available 17α-hydroxypregnenolone diacetate (1). The chemical synthesis is shown in Scheme 5.

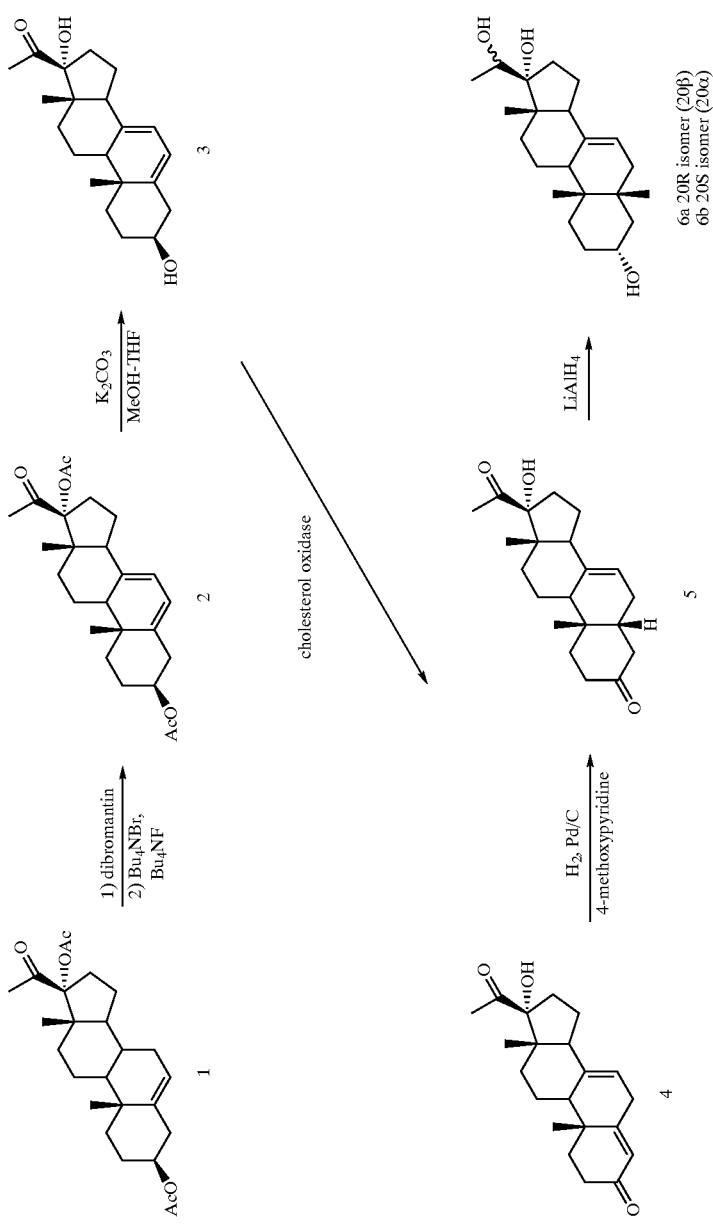

The compound 5β-pregn-7-ene-3α,17α,20R-triol (6a) may be prepared from 17α-hydroxypregneneolone diacetate (1), which is commercially available, by a variety of synthetic routes using synthetic chemical techniques well known to those skilled in the art. In one synthetic approach, shown in Scheme 5 and described more fully in the following examples, 5β-pregn-7-ene-3α,17α,20R-triol was prepared by first forming pregna-5,7-diene-3β,17α-diol-20-one diacetate (2), the 7-dehydro derivative of the hydroxypregneneolone diacetate (1). The diacetate (2) was then hydrolyzed to form the diol 3β,17α-dihydroxypregna-5,7-dien-20-one (3), which was treated with cholesterol oxidase to form the dione 17α-hydroxypregna4,7-diene-3,20-dione (4). The dione (4) in turn was selectively hydrogenated to remove the 4,5 unsaturation and yield the dione 17α-Hydroxy-5β-pregn-7-ene-3,20-dione (5). The dione (5) was reduced to provide the triols 5β-pregn-7-ene-3α,17α,20R-triol (6a) and 5β-pregn-7-ene-3α,17α,20S-triol (6b).

An exemplary scheme for synthesis of 7-DHPT is described in the Examples below.

Methods of Diagnosis Using SLOS Analytes

In one embodiment of particular interest, the invention relates to a method for diagnosis of on SLOS subject. By "SLOS subject" or "SLOS-affected subject" is meant an individual with the SLOS disorder or a woman carrying a fetus affected with SLOS. Prenatal diagnosis of SLOS is of particular interest SLOS diagnosis can be performed by detecting an amount of an SLOS analyte and an amount of a normal steroid counterpart, and determining the ratio of SLOS analyte to steroid counterpart By "normal steroid counterpart" is meant steroid with a chemical structure that differs from the SLOS in that it does not contain a double bond at the position in question. e.g., is the saturated form of the analyte (e.g., the form of the analyte prior to metabolism). For example, a normal steroid counterpart of 8-$DHE_3$ would be $E_3$ which has an identical structure to 8-$DHE_3$ except that it lacks the double bond at carbon-8.

In one embodiment, the SLOS analyte is 8-$DHE_3$. In this embodiment, the preferred steroid counterpart is estriol ($E_3$). In another embodiment, the SLOS analyte is 7-DHPT. In this latter embodiment, the preferred steroid counterpart is pregnanetriol (PT).

Subjects who are of interest for diagnosis according to the methods of the present invention include any subject, including fetuses, which may be suspected of being affected by SLOS. Of particular interest is the screening of pregnant women who are suspected of having an SLOS-affected fetus, particular pregnant women have previously had an SLOS-affected child or carried an SLOS-affected fetus, and thus are "at risk" of having another SLOS-affected child or carrying another SLOS-affected fetus. Other subjects of interest for diagnosis include individuals, such as children and adults, in whom a diagnosis of SLOS is suspected.

Biological samples for analysis according to the method of the invention include any samples suspected of containing the SLOS analyte. The biological sample can be obtained from an adult, a child, in order to facilitate a diagnosis of SLOS. In the context of prenatal diagnosis, the sample is preferably maternal, ie., does not require access to fetal tissues or amniotic fluid. Samples obtained by non-invasive means are of particular interest Exemplary samples include, but are not necessarily limited to urine, blood, serum, plasma, and other blood-derived samples from a patient.

In certain embodiments, SLOS diagnosis can be performed by detecting two SLOS analytes in relation to their normal (e.g., saturated) steroid counterparts, and determining the ratios of SLOS analyte to steroid counterpart for the two SLOS analytes to further minimize the number of false positives.

In the context of prenatal diagnosis, the biological sample can be obtained as early as about 10 weeks or 11 weeks gestation for detecting 7-DHPT in a biological sample such as urine and serum and as early as about 12 weeks gestation for the detection of 8-$DHE_3$ in similar samples. For patients that are at risk, the SLOS diagnostic test of the invention can be performed at a time which is much earlier than the timeline for performing the standard "triple marker" test which occurs around about the 17th week of gestation.

Thus, the 7-DHPT SLOS analyte, and its steroid counterpart PT for determining a ration of 7-DHPT:PT, are useful for early detection of an SLOS-affected fetus from about the $10^{th}$ week of gestation to about the $15^{th}$ week, more usually from about the $11^{th}$ to about the $13^{th}$ week. The 7-DHPT SLOS analyte is also useful in the detection of SLOS during mid-gestation of about the $12^{th}$ to about the $17^{th}$ week of gestation, and more preferably $13^{th}$ to about the $16^{th}$ week of gestation. Of particular interest is prenatal diagnosis of SLOS within or prior to the end of the first trimester.

The 8-$DHE_3$ SLOS analyte is useful in the detection of SLOS during mid-gestation about the $10^{th}$ week or $11^{th}$ week of gestation to about the $17^{th}$ week, usually from $12^{th}$ week of gestation to about the $16^{th}$ week, generally from about the $13^{th}$ to about the $15^{th}$ week. Again, prenatal diagnosis of SLOS within or prior to the end of the first trimester is of particular interest.

In certain embodiments, the diagnostic method comprises obtaining about 1 ml of urine and extracting conjugated steroids using a C18 cartridge. The steroids are eluted from the cartridge with methanol and the methanol is dried. The steroid conjugates are dissolved in acetate buffer and hydrolysed for about three hours at about 55 degrees. The now unconjugated steroids are extracted at least once more with the C18 cartridge and then dried. A known amount of an internal standard, such as stigmasterol is added to the sample and then the sample is subjected to chemical derivatization to make the methyloxime trimethylsilyl ether steroid derivatives. This derivative of urinary steroids is analysed by the gas chromatography/mass spectroscopy (GC/MS) and the quantity of all SLOS specific analytes is measured relative to the internal standard.

In other embodiments, the internal standard is omitted and the sample is compared to a chemically synthesized SLOS analyte compound of a known concentration.

The SLOS diagnostic methods of the invention can provide for accurate diagnosis of SLOS without the need for additional assays, such as assaying for creatinine in urine samples, which is typically done for other steroid assays. When urine is utilized as a sample, the concentration of the urine can be standardized to take into account the varying quantity of water each sample may contain. In typical analyses, steroid values are measured per gram of creatinine, the excretion of which is assumed to be constant per day for ever human. Thus the diagnostic methods of the present invention, e.g. utilizing either the ratio of 7-DHPT/PT and/or 8-$DHE_3$/$E_3$ in a sample or comparing 7-DHPT and/or 8-$DHE_3$ in a sample to 7-DHPT and/or 8-$DHE_3$ standards of known concentrations, eliminates the need for a second assay for creatinine, thus simplifying and reducing the costs of diagnostic testing for SLOS.

Detection of the SLOS analyte and the relevant steroid counterpart in the biological sample can be accomplished by any suitable means. Steroids in general are detected in a biological sample by modifying the steroids in a manner which allows LX them to be analyzed by gas chromatography (GC), gas chromatography followed by mass spectroscopy (GC/MS), high pressure liquid chromatograph (HPLC) or HPLC followed by MS (HPLC/MS). Any other method of steroid detection, either by direct steroid detection or detecting steroid derivatives in a sample, that sufficiently quantifies the SLOS analyte and the relevant steroid counterpart in the sample can be implemented in the SLOS diagnostic methods of the invention. Exemplary methods for determining the amount of the SLOS analyte in a sample may take the form of subjecting the compound being subjected to MS after being eluted from any GC, HPLC or capillary electrophoresis (CE) column useful in the separation of steroids or derivatized steroids from a biological sample, and quantitating the intensity of characteristic mass spectroscopy ion peak(s) for that compound.

In certain embodiments the method of analyzing for the SLOS analytes and the steroid counterpart is by the use of gas chromatography-mass spectrometry. In other embodiments the analysis is completed by the use of high-performance liquid chromatography-mass spectrometry.

In certain embodiments, a ratio of the amount of SLOS analyte to relevant steroid counterpart is determined and compared to a threshold ratio value for SLOS which has been predetermined by testing a number of SLOS patients and normal patients. For prenatal testing the threshold ratio value for 7-DHPT/PT or 8-DHE$_3$/E$_3$ in serum (or other blood-derived sample) and urine ranges from about 0.001 to about 0.03, preferably from about 0.008 to about 0.02 and more preferably from about 0.01 to about 0.015. A ratio that is above these threshold values is indicative of SLOS.

Diagnosis of SLOS can be based upon the detection of a single SLOS analyte (i.e., either 8-DHE$_3$ or 7-DHPT) and the relevant control steroid counterpart or upon detection of both SLOS analytes described herein.

In certain embodiments, the SLOS diagnostic method may comprise utilizing chemically synthesized 7-DHPT and/or 8-DHE$_3$ isolated compounds to calibrate the instrumentation used for the diagnostic assay to ensure accurate detection of these SLOS analytes in patient samples. While other steroids may be used for calibration for analysis instrumentation such as gas chromatography/mass spectrometry (GC/MS), those skilled in the art of GC/MS analysis would confer that the best calibration standard is a purified and synthesized sample of the compound to be analyzed. Thus, the diagnostic method of the invention may comprise both calibrating the analysis instrument with a chemically synthesized SLOS analyte and then completing the analysis by determining the ratios of the SLOS analyte/normal steroid counterpart as stated above. In another embodiments, the samples are prepared and/or derivatized for analysis by HPLC/MS instrumentation instead of GC/MS.

The SLOS diagnostic assays can be performed in conjunction with other tests for SLOS, and may serve as a confirmation of a diagnosis based upon phenotypic presentation of a subject For example, in the context of prenatal diagnosis, the SLOS diagnostic test described herein may be performed where fetal development indicates possible developmental abnormalities such as poor growth, developmental delay, and a common pattern of congenital malformations including cleft palate, genital malformations, and polydactyly (extra fingers and toes).

The ordinarily skilled artisan upon reading the present specification can readily design kits for use in diagnosis of SLOS. Such SLOS diagnostic kits can comprise, for example, at least one synthesized and isolated standard compound which is a SLOS analyte, where the SLOS analyte is 8-DHE$_3$ or 7-DHPT. The "standard compound" is used to calibrate the instrumentation used in the diagnostic assay, such as the calibration of GC and/or GC/MS instrumentation prior to running the assay. The "standard compound" can be used to produce a calibration curve of the SLOS analyte for quantitating the levels of SLOS analyte found in a sample.

The "standard compound" in some embodiments is not the SLOS analyte compound but is a derivatized SLOS analyte compound which is appropriate for the instrumentation utilized in the SLOS diagnostic assay. An exemplary "standard compound" for GC/MS analysis would be a tris-trimethyl silyl (TMS) ether derivative of 8-DHE$_3$. Where desired the kit can contain both compounds, 7-DHPT and 8-DHE$_3$ or derivatives thereof. The kit can further contain instructions for analysis of the SLOS analyte in a biological sample from a subject The kit may also comprise instructions for instrument calibration, sample preparation and protocols for completing the SLOS analysis and data interpretation. The kit can further comprise solutions for the preparation of biological samples for SLOS analysis.

When multiple samples are analyzed for SLOS analytes by GC/MS within a specific time period, such as 4 hours, 8 hours etc., calibration standards are analyzed to insure accurate results from the instrumentation. Prior to analyzing multiple patient samples, a standard mixture comprising PT, 7-DHPT(synthesized), estriol and 8-DBE$_3$ in known concentrations maybe ran to allow the GC/MS instrument to measure the steroids in this standard mixture to set response values based on the known concentrations of the steroids in the standard mixture. The standard mixture may also be ran at the end of the time period as well as during the time period for the multiple sample runs for a more reliable SLOS diagnosis. The standard mixture enables the multiple patient samples to be analyzed using the stored standard values for PT, 7-DHPT, E$_3$ and 8-DHE$_3$ as a callibrant, and reports quantitative values per volume of biological sample analyzed. A data system maybe configured to determined the ratio of abnormal SLOS metabolites (7-DHPT and 8-DHE$_3$) to normal components (PT and E$_3$, respectively) which is the information needed to determine whether a patient is affected with SLOS or carrying a SLOS affected fetus.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1
Diagnostic Screening Method for SLOS Utilizing 8-DHE$_3$ and 7-DHPT

This example demonstrates the detection of 8-dehydroestriol (8-DHE$_3$) and a 7-dehydropregnanetriol (7-DHPT), probably synthesized from fetal 8- and 7-DHC, respectively in urine from SLOS-affected pregnancies. These analytes are the basis for the method of the present invention for a non-invasive early to mid-pregnancy test for SLOS. Presented are data on the measurement of these and related compounds in SLOS affected and SLOS at risk but unaffected pregnancies.

Patients

Thirteen pregnancies at risk for SLOS were included in the study. All had dehydrocholesterols (DHCs) measured in chorionic villus cells or amniotic fluid between the 10th and 31st gestational weeks. Serum $uE_3$ values were known for 11 of the individuals from triple marker screening. Random urine samples were collected between the 12th and 31st weeks, 10 being between the 15th and 20th week. On 6 of the individuals, serum samples were also collected at the time of urine collection. Urine creatinine concentrations were determined. Samples were collected with informed consent approved by the human studies committee of the Johns Hopkins Medical Institutions.

Steroid analytical methodology

Urine extraction. Two ml of urine was analyzed according to a method previously described (Shackleton 1993 *J Steroid Biochem Mol Biol* 45:127–140; Glass et al. 1998 *Prenat. Diagn* 18:789–800) with one alteration. Prior to enzyme hydrolysis, the urine was extracted by $C_{18}$ Sep-pak cartridge and the methanol eluate dried before 3 ml of 0.1 M acetate buffer (pH 4.5) was added together with the Helix pomatia (β-glucuronidase/sulphatase) enzyme preparation. The hydrolysis and all steps following were as described in the publications. The final samples placed in the autosampler contained trimethylsilyl (TMS) and methyloxime-trimethylsilyl ethers (MO-TMS) of all urinary steroids, including 2.5 μg of three internal standards, 5α-androstane-3α,17α-diol, stigmasterol and cholesteryl butyrate. Only stigmasterol was used for quantification, while the other standards were used to monitor column and instrument performance. The standard procedure as described takes approximately 24 hours from sample receipt to data interpretation.

Serum extraction. Serum (0.5–1.0 ml) was diluted to 5 ml with water prior to being heated to 60° for 15 minutes and extracted with a Sep-pak cartridge. The hydrolysis procedures were the same as for urine except that only 1/5 of the enzyme preparations was used and only 0.25 μg of the internal standards were added prior to derivatization.

Gas chromatography/mass spectrometry (GC/MS. Samples were analyzed on a Hewlett-Packard 5971 MSD instrument housing a 15 meter DB1 fused silica capillary column. The operating conditions were described previously (Shackleton 1993, supra; Glass et al. 1998, supra). Quantitation was by selected-ion-monitoring (SIM). In principal, a derivatized mixture of known amounts of reference steroids of most of the compounds to be measured, with internal standards, was analyzed periodically during instrument operation as the instrument calibrator. The principal components of this standard mixture were pregnanediol, pregnanetriol and estriol, and these were present in equal amount to the internal standard. The designated ions for each of the analytes were calibrated against the monitored ion of the primary internal standard, stigmasterol. Once the data system had registered the relative response of each analyte to the internal standards, the amount of each steroid in the serum and urine sample could be automatically reported, and these values corrected to reflect the volume of serum analysed or creatinine concentration of the urine, if known. The data system also reported the diagnostic ratios.

Choice of urine analytes and specific ions used for measurement. Estriol ($E_3$) and 8-dehydro-oestriol ($DHE_3$), the latter being specific for SLOS syndrome, were measured by monitoring $m/z 504$ (M+) and $m/z 412$ (M-90), respectively, of the TMS ethers (FIG. 1). It was ascertained from total iron current (TIC) recordings of scanned runs of a SLOS pregnancy urine extract that the peak area response for the $m/z 412$ of $DHE_3$ (M-90) was almost the same as that of the $m/z 504$ of $E_3$ (M+). Thus, in the absence of a reference steroid, $DHE_3$ could be quantified from the $m/z 412/504$ ratio. It is probable that true values were within 10% of the measured using this calibration.

Pregnanetriol (PT) and 7-dehydropregnanetriol (DHPT) were measured by monitoring $m/z 435$ and $m/z 343$, respectively. In corresponding fashion to the estriols, these ions gave approximately equivalent values when equal amounts of each steroid were analyzed. Thus, in the absence of a reference steroid for 7-DHPT it was quantified by measuring the $m/z 343/435$ ratio. The major progesterone metabolite pregnanediol (PD; monitored ion $m/z 269$) was also determined to ascertain that progesterone synthesis was normal in SLOS affected pregnancies. The excretion of this compound was used as denominator for assessing the adequacy of estriol excretion.

Diagnosis of the patients

As shown in FIG. 2, patients 1–5 were found to have high DHC/cholesterol ratios in amniotic fluid or chorionic villus cells and were diagnosed as having SLOS fetuses. Serum estriol results ($uE_3$) were known for three of these patients and were between 0.14 and 0.23 MOM. Patients 6–13 had normal DHC/cholesterol ratios and were deemed negative for SLOS. They had estriol (uE3) results between 0.79 and 1.76 MOM with mean of 1.18 MOM. All patients were between the 12th and 31st weeks of pregnancy.

$8\text{-}DHE_3$ and 7-DHPT in urine

All the SLOS positive samples had measurable levels of $8\text{-}DHE_3$ and 7-DHPT, including the patient whose collection was during the 12th week of pregnancy. FIG. 2 reports the levels of all measured compounds in μg/g creatinine. Notably, the levels of pregnanediol (PD) differ little between the SLOS affected and non-affected patients. This is expected since pregnanediol is formed predominantly from placental progesterone, which uses maternal cholesterol as precursor. Its production should not be affected by the fetal enzyme deficiency. The mean pregnanetriol (PT) excretion is lower in SLOS pregnancies, although the PT+7-DHPT values virtually equal the value for PT alone measured in the non-SLOS samples. The mean estriol value is low in SLOS although there is considerable overlap with non-SLOS pregnancies, primarily because of highly variable gestational age. Even when $8\text{-}DHE_3$ is added to $E_3$, the mean values for SLOS are still low, representing 0.15 of the unaffected values. This is comparable to the mean $uE_3$ MOM value of 0.23 reported for 26 affected pregnancies by Bradley et al (Bradley et al 1990 *Am J Med Genet* 82:355–358).

Steroid ratios also could be used for diagnosis in the absence of urine creatinine measurement $8\text{-}DHE_3/E_3$ ratios were between 0.073 and 1.42 for SLOS patients and less than 0.01 for those shown not to have the disorder. The 7-DHPT/PT ratios were between 0.037 and 1.02 for SLOS-positive and less than 0.005 for SLOS-negative pregnancies. The mean $E_3$ and $E_3+8\text{-}DHE_3/PD$ ratios were markedly reduced.

$8\text{-}DHE_3$ and 7-DHPT in serum

Only one SLOS-positive and five SLOS negative serum samples from the 13 monitored pregnancies were obtained. $8\text{-}DHE_3$ and 7-DHPT could readily be measured in the SLOS-positive samples, but were below the detection limit for the SLOS-negative patients. Comparing the estriol concentrations between "affected" and "non-affected" samples is not informative because of the small sample number and non-equivalent gestational ages. It must be noted that the values do not represent $uE_3$ as we hydrolysed the sulphate and glucuronide conjugates so these are included as well as unconjugated estriol.

Discussion

This example demonstrates a method of screening patients for SLOS utilizing two of the most important steroids found to be associated with SLOS, 8-dehydro-oestriol ($DHE_3$) and a 7-dehydropregnanetriol (DHPT). The precursors to these steroids had been formed in the fetus from 7- and 8-DHC. Maternal estriol is almost exclusively produced from fetal adrenal precursors, notably dehydroepiandrosterone sulphate (DHEA-S), which is itself synthesized in the fetal adrenal from fetal cholesterol. With the excessive production of 7-DHC and 8-DHC by SLOS fetuses, end products such as 8-dehydro-oestriol ($8\text{-}DHE_3$) and 7-dehydropregnanetriol (7-DHPT) were produced by the fetus and found in maternal biological fluids from an affected pregnancy.

The position of the additional unsaturation within these compounds has been determined to be $8\text{-}DHE_3$ and 7-DHPT with 8-DHC and 7-DHC presumed to be the precursors, respectively.

With the definitive ring B configuration of these steroids ascertained, their distinctive structures and differing molecular weight allow for the calibration of the assay for these compounds which means that they can be commercially used as diagnostic analytes for SLOS. The low level occurrence of these compounds in normal pregnancy urine shows that they cannot be formed biochemically except from 7- and 8-dehydroprecursors, i.e., dehydration of a conventional steroid is not an option. This method has been designed for the quantitation of $8\text{-}DHE_3$ and 7-DHPT as well as their ring B saturated analogues (estriol and pregnanetriol) as well as other reference urinary steroids and used it for retrospective confirmation of the diagnosis of SLOS in 5 out of 13 samples from patients at-risk for the disorder. These five had been previously diagnosed by the finding of elevated DHC/cholesterol ratios in amniotic fluid or cultured chorionic villus cells.

The most important finding in this study was that elevated 7-DHPT/PT and $8\text{-}DHE_3/E_3$ ratio in urine was specific and diagnostic for SLOS. All the SLOS-negative patients had $8\text{-}DHE_3{:}E_3$ and 7-DHPT:PT ratios that were at least greater than 0.01, and often greater than 0.1. All the SLOS-negative samples gave ratio values less than 0.01. Notably, elevated ratio values were detected in a sample collected at the 12th week of gestation, demonstrating that diagnosis can potentially be made at the earliest time reported for the fetal adrenal becoming significantly active.

There exists the possibility of false positives such as mild elevations of the two SLOS analytes in heterozygotes for a null DHCR7 mutant but presently no difference is seen between the analyte levels for heterozygotes or normal individuals.

A serum sample could only be obtained from one affected patient, but 7-DHPT and $8\text{-}DHE_3$ was readily detected in that sample as shown in FIG. 3. Thus, serum analysis can be utilized for diagnosis, which may be an advantage in pregnancies not known to be at risk since in many cases samples already exist from triple marker screening. Based on the reported results, we propose that the $8\text{-}DHE_3/E_3$, with or without the 7-DHPT/PT ratio be included in the primary investigation of patients at risk for SLOS. This would include patients who had a previous child with the disorder, but could be expanded to all pregnant individuals with a low mid-pregnancy estriol ($uE_3$) value.

This methodology can also be used to measure the proposed analytes in at-risk urine samples which are dried on filter paper. The dried samples allow for this method of screening for SLOS to be an analytical procedure which is accessible worldwide. The data from the urine samples dried on filter paper are excellent and could be readily used to confirm the disorder. 7-DHPT and $8\text{-}DHE_3$ are the end products of catabolism and are stable, particularly when conjugated.

Example 2

Identification and Chemical Synthesis of $8\text{-}DHE_3$

Further validation of the non-invasive SLOS diagnostic methods of the invention involved the characterization, identification and production of authentic standards of estrogen metabolites unsaturated in ring B, structures (3) and (4), $7\text{-}DHE_3$ and $8\text{-}DHE_3$, respectively. It should be noted that these dehydroestriols are also of interest as candidate metabolites of equine steroids contained in Premarin®, which is widely used in estrogen replacement therapy ((a) Bhavnani, B. R. *Proc. Soc. Exp. Biol. Med.* 1998, 217, 6–16. (b) Bhavnani, B. R.; Cecutti, A. *J. Soc. Gynecol. Investig.* 1995, 2, 424 (Abstract No. 415).

In general, the synthesis of $8\text{-}DHE_3$ was completed by converting Equilin (8) in three steps to 7-dehydroestriol, which was isomerized to 8-dehydroestriol as depicted in Scheme 3. The bromination of equilin with $CuBr_2$ in MeOH gave complex mixtures. 1D and 2D NMR analysis of standards and crude reaction mixtures led to identification of ten bromosteroids, which, together with equilenin and equilin, accounted for >95% of the steroids observed in most reactions. Knowledge of reporter signals for the numerous bromosteroids facilitated byproduct identification and optimization of reaction conditions. Thus, use of 3 equiv. of $CuBr_2$ in methanol led mainly to bromination in ring A, dehydrogenation to equilenins, and rapid conversion of the desired 16-bromosteroids 9a and 9b to dibromides and equilenins (Table 2, entries 1–2). Shorter reaction times and a smaller excess of $CuBr_2$ resulted in large amounts of unbrominated steroids (8 and 10) and low conversion to the desired products (Table 2, entries 3–5).

In THF, the yield of 16-bromoequilins doubled to 21%, but the product still consisted mainly of equilenins and ring A brominated equilins (Table 2, entry 6). However, reaction in $CHCl_3$-EtOAc gave >70% conversion to 16-bromoequilins (Table 2, entry 7), and these conditions were sufficiently reproducible to afford gram quantities of the desired products as a 2:1 mixture of 16α- and 16β-bromo epimers.

Under specific reaction conditions, this mixture was cleanly hydrolyzed to 16α-hydroxyequilin (7) without formation of 16-keto byproducts. Equilin (101 mg) and freshly ground $CuBr_2$ (166 mg) were heated in $CHCl_3$-EtOAc (25 mL each) for 2 h under vigorous reflux (to remove HBr). The crude product (140 mg; 48% 9a, 24% 9b) was stirred for 1.5 h at rt in DMF-water (3:1, total 10 mL) containing 2 equiv NaOH. MPLC on silica gel (EtOAc-hexane 3:7) gave 7 (78 mg, containing some [6,8]material). Attempts to purify 7 by reverse-phase HPLC (MeOH-$H_2O$ 35:65) gave a 19:1 mixture of 7 and its [6,8]analog. Consequently, the equilenins formed during bromination and hydrolysis were removed after reduction of 7 to 3. NMR ($CDCl_3$, 25° C.): 9a δ 0.814 (s), 4.589 (d, 7.3 Hz), 5.449 (m); 9b δ 0.995 (s), 4.263 (t, 8 Hz), 5.500 (m); 7 δ 0.865 (s), 4.420 (d, 8.3 Hz), 5.509 (m). Reduction of 7 with $NaBH_4$ led to the target 7-dehydroestriol (3). Ketol 7 (446 mg) was reduced with $NaBH_4$ (47 mg) in MeOH (25 mL) for 2 h at 0° C. Methanol was removed at <20° C. in a stream of $N_2$ (higher temperatures resulted in formation of 15). Addition of cold saturated $NH_4Cl$ (10 ml) followed by extraction with EtOAc gave 3 (452 mg, 81% purity). HPLC purification (250×21.2 mm $C_{18}$ column, MeOH-$H_2O$ 45:55) of a 50-mg sample gave 3 (35 mg, 99% purity).

TABLE 2

Bromination of equilin (8) with CuBr$_2$:
effects of reaction conditions on product distribution[a]

| | Δ$^7$ | | | Δ$^{8,8}$ | |
|---|---|---|---|---|---|
| 8 | R$_1$ = H | R$_2$ = H | 10 | R$_1$ = H | R$_2$ = H |
| 9a | R$_1$ = αBr | R$_2$ = H | 11a | R$_1$ = αBr | R$_2$ = H |
| 9b | R$_1$ = βBr | R$_2$ = H | 11b | R$_1$ = βBr | R$_2$ = H |
| 9c | R$_1$ = αBr | R$_2$ = Br | 11c | R$_1$ = αBr | R$_2$ = Br |
| 9d | R$_1$ = βBr | R$_2$ = Br | 11d | R$_1$ = βBr | R$_2$ = Br |
| 9e | R$_1$ = H | R$_2$ = Br | 11e | R$_1$ = H | R$_2$ = Br |

| entry | 1 | 2 | 3 | 4 | 5 | 6 | 7 |
|---|---|---|---|---|---|---|---|
| solvent | | | MeOH | | | THF | C-EA[b] |
| CuBr$_2$[c] | 3.0 | 3.0 | 1.6 | 1.6 | 1.6 | 1.0 | 1.2 |
| t (min) | 30 | 90 | 5 | 15 | 30 | 80 | 90 |
| %9a | 10 | 0 | 6 | 9 | 10 | 16 | 48 |
| %9b | 2 | 0 | 2 | 2 | 1 | 5 | 24 |
| %9c | 9 | 4 | 8 | 5 | 4 | 3 | 0 |
| %9d | 11 | 24 | 1 | 2 | 2 | 1 | 2 |
| %9e | 2 | 4 | 0 | 0 | 0 | 0 | 1 |
| %11a | 0 | 0 | 2 | 4 | 5 | 1 | 7 |
| %11b | 0 | 0 | 0 | 0 | 1 | 1 | 3 |
| %11c | 35 | 32 | 19 | 18 | 15 | 16 | 1 |
| %11d | 21 | 30 | 1 | 2 | 2 | 5 | 4 |
| %11e | 5 | 6 | 0 | 1 | 0 | 2 | 2 |
| %8 | 7 | 0 | 34 | 20 | 15 | 42 | 6 |
| %10 | 0 | 0 | 17 | 22 | 28 | 1 | 1 |

[a]Product distributions were determined by $^1$H NMR. Desired products (9a and 9b) are highlighted.
[b]Chloroform-ethyl acetate 1:1.
[c]Molar ratio of CuBr$_2$ to 8.

With the intention of synthesizing 8-dehydroestriol (4) by a parallel bromination-hydrolysis-reduction scheme, we prepared 8-dehydroestrone (12) by isomerizing equilin with LiNHCH$_2$CH$_2$NH$_2$ in ethylenediamine (Scheme 6). However, refluxing 12 with CuBr$_2$ in CHCl$_3$-EtOAc resulted in virtually no bromination at C-16 or in ring A, the product consisting of a 1:1:2 mixture of 10, 12, and 9(11)-dehydroestrone.

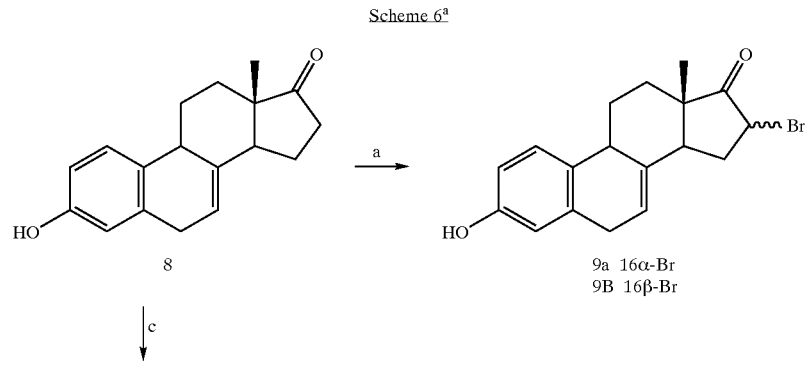

Scheme 6[a]

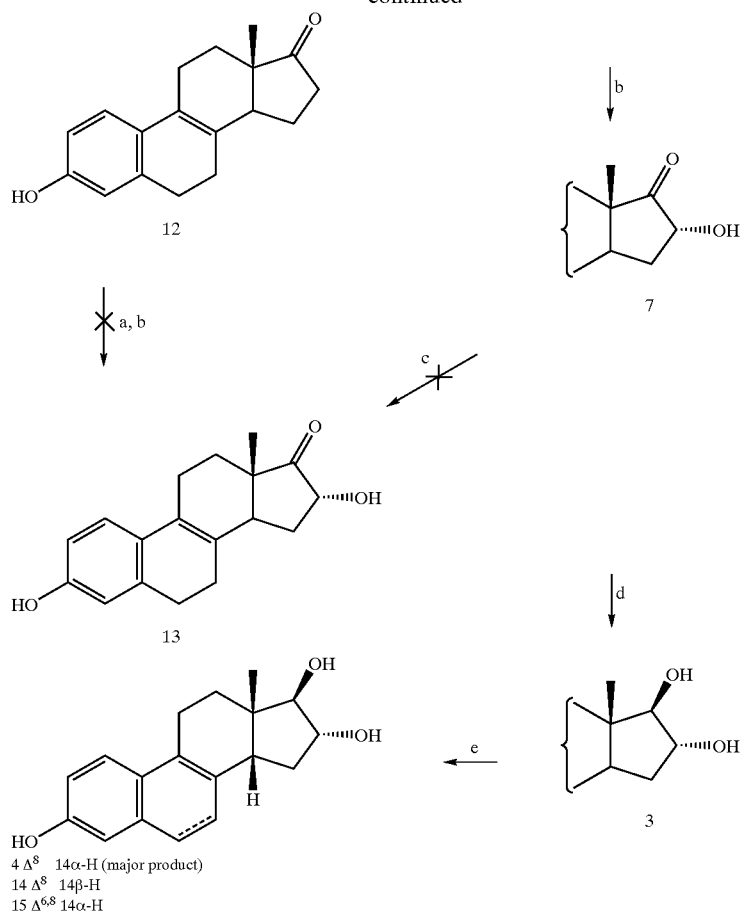

4 Δ⁸ 14α-H (major product)
14 Δ⁸ 14β-H
15 Δ⁶,⁸ 14α-H

An alternative attempt to prepare 13 by LiNHCH₂CH₂NH₂ isomerization of 7 gave none of the expected products. Reaction of 7 (50 mg) with 0.3 M Li in ethylenediamine (3 ml) gave mainly unreacted 7, whereas 1 M Li led to a complex mixture. However, isomerization of triol 3, which lacks the potentially labile 16,17-ketol functionality of 7, was more promising. Despite the poor solubility of 3 and its sluggish rate of isomerization, reaction conditions were found to give 4 as the major product. Dehydroestriol 3 (100 mg) was heated at 40° C. for 48 h in ethylenediamine (3.4 mL) containing LiNHCH₂CH₂NH₂ (prepared by adding 13.4 mmol of MeLi-LiBr in ether to ethylenediamine, followed by evaporation of the ether at 55° C.). NMR of the crude product (104 mg) indicated a 9:5:3:3 mixture of 4, 3, 14, and 15. Preparative HPLC (250×21.2 mm $C_{18}$ column, MeOH-H₂O 35:65, 7 mL/min) gave 14 ($t_R$ 146 min), 15 ($t_R$ 159 min), 3 ($t_R$ 165 min), and 4 ($t_R$ 172 min). NMR (CD₃OD, 25° C.): 3 δ 0.636 (s), 3.578 (d, 5.4 Hz), 4.043 (ddd, 9.1, 5.4, 2.0 Hz), 5.358 (br d, 3.4 Hz); 4 δ 0.757 (s), 3.549 (d, 5.3 Hz), 4.119 (ddd, 9.0, 5.3, 1.8 Hz); 14 δ 0.946 (s), 3.560 (d, 6.9 Hz), 3.999 (ddd, 8.8, 7.9, 6.9 Hz); 15 δ 0.667 (s), 3.668 (d, 5.6 Hz), 4.228 (ddd, 9.1, 5.6, 2.1 Hz). The forcing isomerization conditions resulted in partial epimerization of 4 to 14 and prompted a thorough structure of determination of all products by NMR. In contrast, byproducts were negligible in the preparation of 12 (3% 3, 1% 6-dehydroestrone, and 1–2% 14β steroids) and are frequently absent in base-catalyzed olefin isomerizations. Semipreparative reverse-phase HPLC afforded 4, 14, and 15, which were characterized by 2D NMR and NOE difference spectroscopy to confirm the regio- and stereochemical structure assignments.

With availability of authentic samples of the dehydroestriols, we compared their GC mobilities and mass spectral fragmentation with those of the SLOS urinary metabolites (FIG. 4). FIG. 4 is the GC/MS spectra of tris-TMS derivatives of authentic 7-dehydroestriol (A), 8-dehydroestriol (B), and the dehydroestriol isolated from urine (C). The molecular ions are at m/z 502, and mahor fragments are formed by losses of trimethylsilanol (−90) and methyl groups (−15). GC retention times for A, B and C were 18.77±0.03 min.

Isolation of dehydroestriols

Urine from a pregnant woman carrying an SLOS fetus was processed by standard methods for analyzing urinary steroids: (Shackleton, C. H. L. *J. Steroid Biochem. Mol. Biol.* 1993, 45, 127–140). Briefly, steroid sulfates and glucuronides from a $C_{18}$ solid phase extraction (SPE) of the urine sample were hydrolysed with Helix pomatia (Roman snail) digestive juice (Sigma-Aldrich). The resulting unconjugated steroids were reextracted by SPE and fractionated on Sephadex LH-20 (100×10 mm column; cyclohexane-ethanol 4:1) as described: Setchell K. D.; Shackleton, C. H. L. *Clin. Chim. Acta* 1973, 47, 381–388. GC/MS analysis of individual 5-mL fractions (as TMS ethers) revealed that dehydroestriol was eluted between 140 and 165 mL. The only two steroids found in this fraction were dehydroestriol and didehydroestriol 15. Although the TMS ethers of 7- and 8-dehydroestriols coeluted on the non-polar column used and shared the same parent and fragment ions, the isomers could be distinguished by the relative abundance of these ions. The steroid isolated from urine had the abundance profile of 8-dehydroestriol. This finding does not completely exclude production and excretion of 7-dehydroestriol by SLOS patients since only a few affected individuals have so far been studied. In addition, 7-dehydroestriol is less stable and may undergo aromatization to the didehydroestriol (15) found in urine.

In conclusion, we have developed simple and efficient methods for preparing estrogen metabolites unsaturated in ring B. The availability of these reference dehydroestriols will facilitate the establishment of routine noninvasive prenatal diagnosis for SLOS utilizing 8-DHE$_3$.

Example 3

Chemical Synthesis of 5β-Pregn-7-ene-3α,17α,20R-triol

5β-Pregn-7-ene-3α,17α,20R-triol and its 20S isomer (6a and 6b) were prepared in five steps from the commercially available 17α-hydroxypregnenolone diacetate (1). The chemical synthesis is shown in Scheme 5. A detailed description of one embodiment of the chemical synthesis of 7-DHPT is described below.

Source of reagents

Reagents, including dibromantin, tetrabutylammonium bromide, tetrabutylammonium fluoride, cholesterol oxidase, catalase, and 4-methoxypyridine-N-oxide were obtained from Sigma-Aldrich (Milwaukee, Wis.). 4-Methoxypyridine was obtained by hydrogenation of 4-methoxypyridine-N-oxide over Raney nickel. Solvents were Omnisolve grade from EM Science (Gibbstown, N.J.).

Pregna-5,7-diene-3β,17α-diol-20-one diacetate (2)

To a solution of 17α-hydroxypregnenolone diacetate (1; 2.03 g, 4.8 mmol) in benzene-hexane 1:1 (120 ml) was added dibromantin (0.84 g, 2.92 mmol, 1.2 equiv.) and AEBN (32 mg). The mixture was refluxed under nitrogen for 10 min in a preheated 100° C. oil bath and then placed in an ice bath to cool. The insoluble materials were removed by suction filtration. The reaction flask and the insoluble materials were washed with an additional 20 ml of benzene. The filtrate was concentrated to a yellow solid using a rotary evaporator at 35° C. To a solution of this yellow solid in anhydrous THF (40 ml) was added tetrabutylammonium bromide (0.4 g). The resulting solution was stirred for 75 min under nitrogen at room temperature.

To this reaction mixture was added tetrabutylammonium fluoride (10 ml, 1 M solution in THF, 10 mmol, 2.1 equiv.). The resulting dark brown solution was stirred for an additional 50 min, followed by evaporation to a brown solid using a rotary evaporation at 40–45 ° C. A solution of this solid in ethyl acetate (200 ml) was washed with three portions of water (50 ml each) and dried over anhydrous Na$_2$SO$_4$. The evaporation of solvent gave crude 2 (2.03 g), which was subjected to MPLC (230–410 mesh silica gel; 370×25 mm i.d. column; elution with hexane-ethyl acetate 95:5, 4000 ml and hexane-ethyl acetate 92:8, 2000 ml). Fraction volumes were 20 ml. Fractions 29–42 gave an unidentified byproduct (34 mg). Fractions 161–173 gave pure unreacted starting material (1; 60 mg). Fractions 184–198 gave a mixture of 2 and starting material. Fractions 199–257 gave 2 (0.97 g, 49%) of ca. 95% purity (containing 0.5–2.5% each of several minor olefins). $^1$H NMR (CDCl$_3$), δ 0.587 (s, 3H), 0.949 (s, 3H), 2.075 (s, 3H), 4.715 (m, 1H), 5.451 (m, 1H), 5.577 (m, 1H).

3β,17α-Dihydroxypregna-5,7-dien-20-one (3)

To a solution of diacetate 2 (100 mg) in a 1:2 mixture of tetrahydrofuran and methanol (24 ml) was added potassium carbonate (140 mg). The resulting mixture was sparged with nitrogen and then stirred at room temperature under nitrogen for 46 h. After completion of the reaction as judged by TLC, water (60 ml) was added. The resulting mixture was extracted with ethyl acetate (2×60 ml). The combined organic phase was washed with water (2×30 ml) and dried over anhydrous Na$_2$SO$_4$. Evaporation of solvent gave a white solid (64 mg), which was dissolved in methanol and precipitated by addition of water to give a white solid (56 mg, 71% yield) of high purity.

17α-Hydroxypregna4,7-diene-3,20-dione (4)

A solution of 3 (25 mg, 0.075 mmol) in butyl acetate (7 ml) was added to a TES buffer solution (6 ml, 50 mM, pH 7.5) containing cholesterol oxidase from Streptomyces species (50 units, 2.6 mg, 19 units/mg solid) and catalase (31 uml, 25 mg/ml, 51100 units/mg, 40000 units). The two-phase mixture was stirred in a vial at room temperature with a magnetic stirrer for 17 h. Ethyl acetate (20 ml) was added to the reaction mixture, and the separated organic phase was washed with water and brine, and dried over Na$_2$SO$_4$. Evaporation of solvent gave crude 4 (24 mg) as a nearly colorless solid.

17α-Hydroxy-5β-pregn-7-ene-3,20-dione (5)

To a solution of 4 (20 mg) in 4-methoxypyridine (1.5 ml) was added palladium on carbon (20 mg, 10% palladium by weight). The resulting mixture was stirred at room temperature under a hydrogen-filled balloon for 16 h. The catalyst was filtered through a cotton-plugged pipette containing Celite. Removal of solvent by bulb-to-bulb distillation gave crude 5 (20 mg) as a nearly colorless solid.

5β-Pregn-7ene-3α,17α,20R-triol(6a) and 5β-pregn-7-ene-3α,17α,20S-triol (6b)

To a solution of 5 (20 mg) in ether (5 ml) was added LiAlH$_4$ (50 mg). The resulting mixture was refluxed in a 55 deg C. oil bath for 2 h, followed by addition of cold 5% HCl (5 ml) to quench the reaction. The organic phase was separated, washed product (21 mg) comprising a mixture of C-20 epimers 6a and 6b. A portion (10 mg) of this mixture was subjected to preparative reverse-phase HPLC using a Phenomenex Prodigy 5 u ODS(3) column (250×21.2 mm, UV detection at 210 nm). Elution with 80% MeOH in water (9 ml/min) gave homogenous samples of the 20R isomer 6a (3.4 mg, $t_R$ 21.1 min) and the 20S isomer 6b (3.1mg, $t_R$ 23.1 min).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of prenatal diagnosis of a fetus affected by Smith-Lemli-Optiz syndrome (SLOS) comprising:

obtaining a biological sample from a woman suspected of carrying an SLOS-affected fetus;

analyzing the sample for a at least one specific SLOS analyte and a control steroid counterpart, wherein the SLOS analyte is selected from the group consisting of 8-dehydro-estriol (8-DHE3) and 5β-pregn-7-ene-α,17α,20α-triol (7-DHPT); and determining the ratio of the SLOS analyte to the control steroid counterpart found in the sample;

wherein a ratio of greater than 0.01 indicates that the woman carries an SLOS-affected fetus.

2. The method of claim 1, wherein the biological sample is a urine sample.

3. The method of claim 1, wherein the biological sample is serum.

4. The method of claim 1, wherein the sample is a blood or blood-derived sample.

5. The method of claim 1, wherein said analyzing comprises analysis by use of gas chromatography-mass spectrometry.

6. The method of claim 1, wherein said analyzing is by use of high-performance liquid chromatography/mass spectrometry.

7. The method of claim 1, wherein the biological sample is obtained as early as about the 11th week of gestation.

8. The method of claim 1, wherein the SLOS analyte is 8-DHE3 and the steroid counterpart is a estriol ($E_3$).

9. The method of claim 1, wherein the SLOS analyte is a 7-DHPT and the control steroid counterpart is a 5β-pregnane-3α,17α,20α-triol (PT).

10. The method of claim 1, wherein each of the SLOS analytes 8-$DHE_3$ and 7-DHPT are detected.

\* \* \* \* \*

UNITED STATES PATENT AND TRADEMARK OFFICE
CERTIFICATE OF CORRECTION

| | | |
|---|---|---|
| PATENT NO. | : 6,808,932 B1 | Page 1 of 1 |
| APPLICATION NO. | : 10/077577 | |
| DATED | : October 26, 2004 | |
| INVENTOR(S) | : Cedric Shackleton | |

It is certified that error appears in the above-identified patent and that said Letters Patent is hereby corrected as shown below:

In column 1 line 9: Delete "may have" and replace with "has".

Signed and Sealed this
First Day of March, 2011

David J. Kappos
*Director of the United States Patent and Trademark Office*